(12) United States Patent
Lub (10) Patent No.: US 6,660,344 B2
(45) Date of Patent: Dec. 9, 2003

(54) POLYMERIZABLE LIQUID CRYSTALLINE DIOXETANES, THEIR PREPARATION AND USE

(75) Inventor: Johan Lub, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 28 days.

(21) Appl. No.: 09/969,700

(22) Filed: Oct. 3, 2001

(65) Prior Publication Data

US 2003/0111640 A1 Jun. 19, 2003

(30) Foreign Application Priority Data

Oct. 4, 2000 (EP) .............................. 00203459

(51) Int. Cl.⁷ ........................ C09K 19/34; C09K 19/38; C07D 305/06; G02F 1/1333
(52) U.S. Cl. ............. 428/1.1; 252/299.61; 252/299.67; 549/510; 549/511; 349/88; 349/183; 528/417
(58) Field of Search ...................... 252/299.01, 299.67, 252/299.5, 299.61; 428/1.1; 549/510, 511; 349/10, 86, 88, 183; 528/417

(56) References Cited

U.S. PATENT DOCUMENTS 5,188,760 A  2/1993  Hikmet et al.  .........  252/299.01

FOREIGN PATENT DOCUMENTS

| EP | 0552508 | 6/1997 | ......... G02F/1/1333 |
| EP | 1069120 A1 | 1/2001 | ......... C07D/305/06 |
| JP | 11106380 | * 4/1999 | |
| WO | WO9522586 | 8/1995 | ......... C08K/239/34 |
| WO | WO9524454 | 9/1995 | ............ C09K/9/38 |
| WO | WO9524455 | 9/1995 | ........... C08K/19/38 |
| WO | WO9700600 | 1/1997 | |
| WO | WO9847979 | 10/1998 | ........... C08K/19/20 |
| WO | WO9943763 | 9/1999 | ........... C09K/19/38 |

OTHER PUBLICATIONS

Englisg Abstract for JP 11–106380, http://www6.ipdl.jpo.go.jp/Tokujitu/PAJdetail.ipdl?N0000=60&N0120=01&N2001=2&N3001=H11–106380.*
XP–002190289, Section CH, Week 199926, Database WI, Derwent Publications Ltd., London, GB; AN 1999–308089, & JP 11 106380 A (UBE Ind Ltd), Apr. 20, 1999 Abstract.
Hikmet R.A.M. et al., Prog. Pol. Sci. 21:1165–1209(1996) "Anisotropic Networks and Gels Obtained by Photopolymerisation in the Liquid Crystalline State: Synthesis and Applications".
Yusuke Kawakami et al, Macromolecules 24:4531–4537 (1991) "Synthesis of Liquid Crystalline Polymers with a Polyoxetane Main Chain".
Yusuke Kawakami et al, Polymer Bulletin 25:439–442 (1991) "Smectic Liquid Crystalline Polyoxetane with Novel Mesogenic Group".
Polymer International 31: 35–40 (1993) "Synthesis and Thermal Transition of Side–chain Liquid Crystalline Polyoxetanes Having Laterally Attached Mesogenic Group".
Japanese Abstract; JP–A–06308462 "High–Polymer Liquid Crystal and Liquid Crystal Element Formed by Using the Same"; Nov. 4, 1994.
Japanese Abstract: JP–A–08020641 High–Molecular Liquid Crystal and Liquid Crystal Element; Jan. 23, 1996.
Japanese Abstract: JP–A–08301859; "Oxetane compound and Its Polymer" Nov. 19, 1996.
Lu Y.–H., et al., Polymer Bulletin, 32:551–448 (1994); "Synthesis of Side–Chain Liquid Crystalline Polyoxetanes Containing 4–Dodecanyloxyphenyl Trans–4–Alkylcyclohexanoate Side Groups".
Macromolecules 28:1673–1680 (1995); "Synthesis of Side–Chain Liquid Crystalline Polyoxetanes Containing 4–(Alkanyloxy) Phenyl Trans–R–Alkylcyclohexanoate Side Groups".
H. Ogawa, et al., Bull. Chem. Soc. Jpn. 70: 1649–1657 (1997); Side–Chain Liquid–Crystalline Polyoxetanes with a Spacer–Separated Azobenzene Moiety. III. Preparation and Characterization of Polyoxetanes Anchoring the Mesogen Cores of a p–Spacer–Substituted Phenyl 4–(4–Alkoxyphenylazo) benzoate in the Side Chain.
Japanese Abstract; JP–A–07225370; Aug. 22, 1995; "Liquid Crystal Element and IRTS Production".

* cited by examiner

Primary Examiner—Shean C. Wu (57) ABSTRACT

New photopolymerizable liquid crystalline dioxetane compounds are provided having the general formula I:

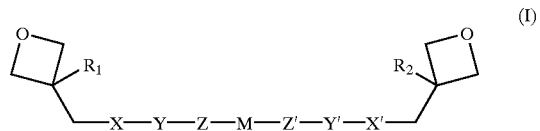

wherein $R_1$ and $R_2$ are independently selected from straight or branched $C_1$–$C_4$ alkyl and hydrogen; X and X' are independently selected from oxygen, sulfur, a single covalent bond, —O—CO—, —CO—O—, and —O—CO—O—; Y and Y' are spacer groups having each independently 1 to 30 carbon atoms (linear or branched), in which the carbon chain may be interrupted by oxygen in the ether function or by sulfur in the thioether function; Z and Z' are independently selected from oxygen, sulfur, a single covalent bond, —O—CO—, —CO—O—, and —O—CO—O—; and M is any suitable mesogenic group.

Also, compositions are provided containing one or more compounds of formula I, as well as methods of preparing said compounds and compositions. These compounds and compositions show excellent characteristics upon polymerization, such as improved non-shrinking properties, and are useful in a variety of applications, in particular in liquid crystal devices, sensors, and optical precision instruments.

12 Claims, 1 Drawing Sheet

POLYMERIZABLE LIQUID CRYSTALLINE DIOXETANES, THEIR PREPARATION AND USE

This present invention generally relates to a new class of liquid crystalline monomers and polymers. More in particular, it describes polymerizable dioxetane compounds which are capable of forming liquid-crystalline polymeric networks with advantageous properties which make them useful inter alia in optical display units (LCDs).

Oriented structures are of great interest due to their anisotropic properties. Such structures can possess highly anisotropic optical, electrical and thermo-electrical properties which are desirable for various applications.

Liquid-crystalline (LC) molecules combine liquid-like properties such as low viscosity, with crystal-like properties such as anisotropy. LC phases are observed between the melting temperature and the anisotropization temperature. There are various LC phases with different kinds of ordering, of which the nematic an cholesteric phases are of special interest. In the nematic phase, only a degree of orientational order is present and the molecules tend to orient their long axis along a common direction ("the director"). In the cholesteric phase, molecules are oriented in nematic layers and the nematic director is rotated around a helix. This phase is obtained by the inclusion of chiral molecules in a nematic system. Characteristic for this phase is the property of selective reflection of a band of circularly polarized light which makes the material looks colored. This property of the cholesteric phase can be used in the production of passive optical components.

In an LC phase, molecules are oriented in small domains. The orientation of these domains can be achieved in an electric field, a magnetic field or on specially treated surfaces. For example, in a sufficiently high electric field (1 V/µm), molecules with a positive dielectric anisotropy can be oriented along the field. Surfaces coated with a polymeric layer which are subsequently rubbed, tend to orient LC molecules along the direction of rubbing. Surfaces treated with surfactants tend to orient LC molecules perpendicular to the substrate. These properties make LC molecules extremely versatile in obtaining any orientation on any surface geometry.

LC phases and the properties of LC systems within a certain phase are highly temperature dependent. Therefore, any attempt to "freeze in" the properties of an LC system by polymerization has to be carried out isothermally. Changes in temperature may result in polymerization in the wrong phase or in a poorly oriented state. For these reasons isothermal photopolymerization, and also e-beam polymerization, of LC molecules are the preferred methods. For the purpose of photopolymerization, LC molecules with polymerizable groups, such as LC acrylates, epoxides and vinylethers are usually employed, together with an appropriate photo-initiator. Using monomers with two or more polymerizable groups will lead to the formation of crosslinked networks with improved thermal and chemical stability. The LC system is heated to the desired temperature and after the disappearance of the domains (induction of long range ordering) polymerization is initiated with a UV-light source or the like, to obtain a three-dimensional network in which the orientation of the molecules and the properties of the desired phase are "frozen in". For further background information, reference may be made e.g. to Hikmet R. A. M. et al., *Prog. Pol. Sci.* 21:1165–1209 (1996).

Recent prior art predominantly discloses LC mono- and diacrylates for use of photopolymerizable liquid crystals in the manufacture of optical components to be used in liquid crystal displays (LCDs). See, for example, WO 96/24647, WO 97/00600, WO 98/47979. Drawbacks of the use of this type of materials frequently include the following: (1) the polymerization reaction is inhibited by oxygen which demands the need of an inert gas during the polymerization process; (2) due to the relatively high crystallization temperatures of the liquid crystals the processing has to be done at high temperatures which makes film making by spincoating nearly impossible due to prior crystallization; (3) the polymer network prepared from acrylates will exhibit stress at room temperature due to polymerization shrinkage, which may also lead to (4) deformation of the optical component in which the polymer network is applied.

In the past decade, various authors disclosed liquid crystalline polyoxetanes based on mono-oxetane monomers, as well as their preparation and properties. See, for example, Kawakami Y., et al., *Macromolecules* 24:4531 (1991), *Polym. Bull.* 25:439 (1991), *Polym. Int.* 31:35 (1993), JP-A-06308462, JP-A-08020641, JP-A-08301859; Lu Y. -H., et al., *Polymer Bulletin*, 32:551–558 (1994), *Macromolecules* 28:1673–1680 (1995); Hsu L. -L., et al., *J. Polym. Sci* 35:2843–2855 (1997); Ogawa H., et al., *Bull. Chem. Soc. Jpn.* 70:1649–1657 (1997); JP-A-07225370.

The ring-opening polymerization reaction of mono-oxetanes, initiated by e.g. a $BF_3$ etherate complex and resulting in side-chain liquid crystal polymers with flexible polymer backbones and broad liquid crystalline phase temperature ranges which extend from room temperature up to 240° C., can be generally depicted as follows:

wherein X generally represents a spacer group, such as an alkylene, an ether-based divalent group, or a siloxane-based divalent group, Y is a mesogenic group, and Z is a chiral group-containing terminal group.

However, the liquid crystalline polyoxetanes based on mono-oxetane monomers appear to suffer from some drawbacks, in that the stability of the alignment of the molecules is not so high due to thermal transitions or crystallization. Furthermore, the alignment of the polymers to obtain domain-free films is difficult due to the relatively high viscosity and the films are not stable to organic solvents.

There is therefore a need for photopolymerizable liquid crystalline compounds and polymerized derivatives thereof that do not have the disadvantages mentioned above, but rather exhibit improved properties, such as being polymerizable in the air, capable of being spincoated at room temperature, aligned easily, and showing very low polymerization shrinkage which would make them useful in a variety of applications.

It has now surprisingly been found that a new class of compounds, photo-polymerizable liquid crystal dioxetanes and/or polymeric products derived thereof show excellent properties which make them useful for application e.g. in liquid crystal mixtures and liquid crystal devices such as liquid crystal displays (LCDs).

Accordingly, the present invention provides in one aspect a compound having the general formula I:

(I)

wherein R$_1$ and R$_2$ are independently selected from straight or branched C$_1$–C$_4$ alkyl and hydrogen;

X and X' are independently selected from oxygen, sulfur, a single covalent bond, —O—CO—, —CO—O—, and —O—CO—O—, Y and Y' are spacer groups having each independently 1 to 30 carbon atoms (linear or branched), in which the carbon chain may be interrupted by oxygen in the ether function or by sulfur in the thioether function;

Z and Z' are independently selected from oxygen, sulfur, a single covalent bond, —O—CO—, —CO—O—, and —O—CO—O—, and M is any suitable mesogenic group.

In another aspect, the invention provides liquid-crystalline compositions comprising one or more of said compounds of formula I, in conjunction with one or more liquid crystalline compounds selected from the group of normal non-polymerizable compounds and mono-oxetane monomers. In a preferred embodiment, said compositions comprise one or more chiral compounds.

In still another aspect, the invention provides a method of preparing the compounds of formula I as defined above, as well as a method of preparing said liquid-crystalline compositions comprising one or more compounds of formula I and, optionally, one or more chiral compounds.

In yet another aspect of the present invention the use is provided of one or more compounds of formula I, or compositions comprising one or more of said compounds of formula I, for the manufacturing, for example, of optical display units, optical precision units, sensors, cholesteric liquid-crystalline coloring agents, and pigments.

These and other aspects will be explained in more detail in the following detailed description and accompanying drawings.

DEFINITIONS

As used herein, the term reactive liquid crystalline compounds refers to reactive rod-like molecules which may be enantiotropic, monotropic or isotropic, preferably, however, enantiotropic. As used herein, the term crosslinked liquid crystalline (co)polymer is meant to indicate an oriented network.

Preferred Compounds of Formula I

Suitable R$_1$ and R$_2$ groups in the compounds of formula I include hydrogen, methyl, ethyl, n-propyl, and n-butyl, of which methyl in particular is preferred.

Preferred values for X and X' groups are oxygen and a direct covalent bond, of which oxygen is preferred.

Preferred spacer groups Y and Y' include predominantly linear aliphatic alkylene chains of up to 30 carbon atoms, preferably 3 to 12 carbon atoms, which may each be branched by one or more, preferably up to five, and more preferably up to three methyl groups; ethylene oxide (C$_2$H$_4$O)$_n$ chains having up to 30 carbon atoms, preferably 3 to 12 carbon atoms, which may each contain one or more branched methyl groups, preferably up to five and most preferably up to three methyl groups. In certain embodiments of the invention the branched methyl groups are desired, since the asymmetric carbon atoms thus created cause a cholesteric (i.e. chiral-nematic) phase which enables interesting optical applications, such as color separation, generation of polarized light, etc. (see Hikmet et al., supra).

Preferred values for Z and Z' groups are oxygen and a direct covalent bond, of which oxygen is preferred.

As mesogenic moieties all known mesogenic groups can be used. For an extensive survey of suitable mesogenic groups, and the preparation thereof, which can also be used in the present compounds of formula I, see e.g. WO 96/24647, WO 97/00600, and WO 98/47979, the contents of which are all incorporated herewith by reference. Thus, suitable mesogenic groups M include groups of the formula II:

(II)

wherein:

Q and Q' are independently selected from the group of divalent saturated or unsaturated iso- or heterocyclic moieties, X" is X or X', or —CH$_2$—O—, —O—CH$_2$—, —N=N—, —N=N(O)—, —CH$_2$S—, —SCH$_2$—, —CO—O—, —O—CO—, or ethylene, and is 0, 1, 2 or 3. If p>1, X" may have the same or different meanings (within the definition).

Preferably, p is 1 or 2. The Q and Q' ring moieties can also be substituted by one, two or three equal or different fluoro, chloro, bromo, cyano, hydroxy, nitro, formyl, C$_{1-10}$ alkyl, C$_{1-10}$ alkoxy, C$_{1-10}$ alkoxycarbonyl, C$_{1-10}$ monoalkylaminocarbonyl, C$_{1-10}$ alkylcarbonyl, C$_{1-10}$ alkylcarbonyloxy groups, in particular when Q and Q' are aromatic moieties, most preferably benzene derivatives.

Preferred Q and Q' moieties include:

Preferred mesogenic groups include, for example:

wherein G' and G" are each independently selected from the group consisting of hydrogen, methyl, fluoro, chloro bromo and nitro. Preferably, G' is methyl and G" is hydrogen.

In a preferred embodiment of the invention a claa of compounds of formula (I) is provided having the formula (I') shown below:

wherein R preferably is methyl, and n preferably is 4, 5 or 6.

According to a further aspect of the present invention, a liquid crystal material is provided comprising at least one compound according to formula I. In still a further aspect of the invention, the liquid crystal material contains one or more asymmetric carbon atoms.

Preparation of the Compounds of Formula I

The literature describes a plurality of synthesis routes for the preparation of polymerizable liquid crystal compounds. The molecules are frequently usually built up from the "exterior" to the "interior", but this will of course depend on the nature of the compounds to be prepared and the preferences of the manufacturer. In such cases, the mesogenic group M is added in the last step to the precursor compounds that already contain the desired reactive or non-reactive (possibly also chiral) groups as well as spacer units to complete the construct.

-continued

All aromatic rings of the above preferred mesogenic groups can have one or more substituents each independently selected from the group consisting of methyl, fluoro, chloro, bromo, and nitro.

Especially preferred are the mesogenic groups of the following formulas:

Suitable and preferred starting materials for preparing the liquid crystalline dioxetanes according to the invention include the following alcohols which are commercially available:

and derivatives of these alcohols such as the following products:

The oxetane compound of choice is then linked to a spacer molecule having a reactive group on the one end which is capable of reacting with a suitable reactive group of the oxetane compound to form a covalent bond, usually through addition, condensation, or substitution, and another reactive group on the other end of the spacer molecule, or a precursor form thereof, which is capable of forming a link to a mesogenic group of choice. A person skilled in the art will have no difficulty in selecting the compounds which are to be linked, as well as appropriate reaction conditions.

As a typical example of the preparation of the compounds of formula I according to the invention, the starting 3-methyl or 3-ethyl-3-hydroxymethyloxetane is converted into a corresponding oxetane compound where the hydroxy group is converted into a more reactive group, for example a tosylate group, in a manner known per se. This terminal reactive group of the side chain of the basic oxetane compound is conveniently reacted with a compound of the type 4-bromophenoxy-alkan-1-ol to form one of the following compounds of the formula III:

wherein $R_1$, $R_2$, X, X', Y, and Y' are as defined before, and Q and Q' each indicate a reactive group (same or different), for example a bromine atom. The resulting compound (or compounds) of formula III is then preferably converted into the corresponding carboxylic acid compound in a manner known per se, for example using a suitable lithium compound, such as n-butyllithium, or through a Grignard compound. In the next stage, the resulting dioxetane derivative(s) having a carboxylic acid group are reacted with a mesogenic precursor compound to form a compound of formula I, or a mixture of such compounds. As mesogenic precursor compounds mesogendiol compounds (HO—M—OH) or similar compounds with reactive groups are advantageously used.

In an alternative typical preparation of compounds of formula I, the starting 3-methyl or 3-ethyl-3-hydroxymethyloxetane is converted into the corresponding haloalkyl-ether oxetane derivative (preferably the bromide compound), which is then reacted with a reactive compound, such as a hydroxybenzoate or similar compound, to form eventually a compound of formula III which is then converted in a compound of formula I (or a mixture of such compounds), as indicated above.

The type of reactions which are advantageously used to prepare compounds of formula I, as well as alternative routes, are well known to the average skilled worker in this art. The selection of the particular dioxetane groups to be used, as well as the particular spacers and mesogenic groups will depend on the choice and preferences of the user and/or the manufacturer. Also the specific reaction conditions, in particular the reaction temperature(s), reaction time(s), reaction pressure(s), and solvent(s) typically depend on the reactants to be used and the preferences of manufacturer. Generally, the overall reaction time will vary between a few minutes and a few days and the reaction temperatures generally will vary from −80° C. to the reflux temperature of the reaction mixture. Preferably, all reactions are carried out at atmospheric pressure. Generally, there is no need to apply a special inert atmosphere for polymerizing the compounds of formula I, in contrast to the polymerization of liquid crystalline acrylates, and the like compounds. A person skilled in the art can easily optimize the reaction conditions in each individual case, without undue experimentation and without any inventive effort.

The reaction schemes mentioned above are to illustrate the invention without restricting it. Further details for the preparation of the compounds of formula I can be found inter alia in WO 95/22586, WO 95/24454, WO 95/24455, WO 97/00600, and WO 99/43763 which are incorporated herein by reference.

Applications

The dioxetane compounds of formula I are conveniently polymerized to form liquid crystalline polymers, preferably by photopolymerization or e-beam polymerization, which methods are well known in the art. Therefore, according to another aspect of the invention, a liquid crystalline material is provided comprising a dioxetane (co)polymer compound substantially derived from one or more dioxetane monomer compounds of the formula I. Since the dioxetane monomers of formula I according to the present invention will contain two (or more) polymerizable groups, the resulting liquid crystalline (co)polymers or liquid crystalline material will also be crosslinked upon polymerization, usually concommittantly, thus creating oriented networks. In a special embodiment, said dioxetane (co)polymers have optically active properties. Advantageously, the liquid crystal material comprises both a compound of formula I and a polymer compound substantially derived from one or more compounds of formula I.

Preferably, a compound of choice of formula I is mixed with a suitable amount of a photoinitiator, for example Cyracure UVI-6990 which is commercially available, in a suitable solvent, such as chlorobenzene, and then applied on a substrate, preferably by spincoating or a similar technique, and photopolymerized using a suitable UV source. Alternatively, a composition of two or more compounds of formula I is mixed together with the photoinitiator to form a dioxetane liquid crystalline copolymer upon radiation.

In yet another embodiment of the invention a composition comprises one or more compounds of formula I (usually two or three compounds) and non reactive liquid crystals or more prior art monomers or oligomers, for example liquid crystals to form liquid crystaline gels, or mono-oxetane monomer or oligomer disclosed in any one of the references mentioned above, to form another liquid crystalline copolymer or polymer mixture, respectively.

The polymerization temperature and reaction time for preparing the various dioxetane polymers disclosed above are not very critical and are usually between room temperature and about 85° C. with reaction times usually in the range of a few minutes to one or two hours, to obtain a conversion of between about 10% and substantially completion. Generally, higher conversion can be obtained by adding an annealing step at higher temperatures, usually between about 100 and 170° C. for about 0.25 to 1 hour, without changing the optical properties.

The dioxetane liquid crystalline (co)polymers of the present invention have excellent characteristics, especially when compared to the state-of-the-art LC polymers. They are preferably used as films in a variety of applications, in particular in optical displays. As stated before, due to the relatively high crystallization temperatures of, for example, liquid crystalline diacrylates, processing has to be carried out at high temperatures which makes film formation by spincoating nearly impossible due to prior crystallization. Also, the polymer network prepared at higher temperatures tends to exhibit stress at room temperature due to thermal shrinkage which, in turn, causes stress and deformation of the optical component concerned. The present invention solves these problems by the provision of these new dioxetane liquid crystal monomers and (co)polymers, liquid crystal mixtures, and liquid crystal devices. The new dioxetane monomers generally have substantially lower crystallization temperatures, as is typically demonstrated in Table 1 in the Examples below, thus avoiding the problems raised with LC polymers of the prior art.

Also, by changing the polymerizable acrylate group into an oxetane group, the polymerization reaction is conveniently carried out in the air rather than in an inert gas, since the polymerization is not inhibited by oxygen. The dioxetane compounds of formula I or compositions comprising one or more dioxetane compounds of formula I are usually dissolved in a suitable solvent and mixed with a suitable cationic photoinitiator. The solution is then spincoated on a substrate, preferably at room temperature or elevated temperature, and the resulting film is polymerized using a suitable UV source. Alternatively, polymerization is carried out with e-beam radiation. The polymerized product shows very low polymerization shrinkage. The volume polymerization shrinkage which is measured can be as low as about 2%, i.e. less than half of the shrinkage during similar acrylate polymerization. The liquid crystalline (co)polymers according to the present invention are therefore particularly useful in situations where low polymerization shrinkage is required such as in lenses. In addition, these polymers have excellent birefringent properties which are temperature independent over a long temperature range.

In a further embodiment of the invention, liquid-crystalline compositions are provided comprising one or more of said compounds of formula I and one or more chiral compounds. Suitable chiral compounds for the purpose of the present invention include, for example, the commercially available products R-811 or S-811 from Merck based on 2-octanol, or the isosorbide based chiral dopant additives described in WO-98/00428. These compositions can be suitably used for the preparation of polymer films with a chiral liquid crystalline phase, for active and passive optical elements (e.g. circular polarizers) or color filters and for liquid crystalline displays, for example STN, TN, AMD-TN, temperature compensation, guest-host, or phase change displays, or polymer free or polymer stablized cholesteric texture (PFCT, PSCT) displays. The present invention also encompasses polymer films with a chiral liquid crystalline phase, obtainable by (co)polymerizing in a known manner a liquid crystalline composition as defined above.

In a further aspect of the invention a display cell is provided comprising two opposite plates which are transparent to light electrodes of a material which is transparent to light on the sides of the plates facing each other, orientation layers on the electrodes, a sealing material between the plates, and a liquid crystalline material being filled into the space between the plates and the sealing material, said liquid crystalline material comprising a polymerizable liquid crystalline material wherein said polymerizable liquid crystalline material is substantially derived from one or more dioxetane compounds of formula 1, or from a composition comprising one or more dioxetane compounds of formula 1, as defined above, which when polymerized forms a permanently oriented network, said permanently oriented network being formed only locally in accordance with a desired pattern, substantially as disclosed in EP-A-0552508, which is incorporated herein by reference.

In still another embodiment, the invention provides a liquid crystalline material in the form of an anisotropic gel comprising a liquid crystalline (co)polymer product which is substantially derived from one or more dioxetane compounds of formula 1, or from a composition comprising one or more dioxetane compounds of formula 1, as defined above, and a non-polymerizable low-molecular weight liquid crystalline material, wherein said liquid crystalline (co)polymer product forms a permanently oriented network in said non-polymerizable low-molecular weight liquid crystalline material. Suitable non-polymerizable low-molecular weight liquid crystalline materials include, for example, those materials referred to as material b) in U.S. Pat. No. 5,188,760, the disclosure of which is herein incorporated by reference. Typical examples of such non-polymerizable low-molecular weight liquid crystalline materials are the compounds (a)–(d) depicted below:

or mixtures thereof. A suitable mixture of the above compounds (a)–(d) is commercially available under the designation E7 from BDH, in quantities of 8%, 51%, 25% and 16%, respectively. It is alternatively possible to use a liquid crystalline material as the non-polymerizable low-molecular weight liquid crystalline material having polymerizable groups which do not or hardly polymerize under the conditions of polymerization of the network comprising one or more dioxetane compounds according to the present invention.

According to still another aspect, the present invention provides a method of making an electro-optical device comprising one or more dioxetane compounds of formula 1 comprising the steps of: (a) forming a cell comprising two cell walls spaced apart, the walls inner surfaces having formed thereon electrode structures; (b) providing a mixture comprising a monomer material comprising one or more dioxetane compounds of formula 1 and a suitable initiator, preferably a photo-initiator; (c) introducing said mixture between the cell walls; and (d) polymerizing the mixture as described above. Preferably at least one wall is surface treated to provide liquid crystal alignment. The monomer material may be aligned in a known manner before polymerization and/or the polymer may be aligned after polymerization. According to an alternative aspect, the present invention provides a liquid crystal device which comprises two spaced cell walls each bearing electrode structures and treated on at least one facing surface with an alignment layer, and a layer of liquid crystal material enclosed between the cell walls, wherein the layer of liquid crystal material comprises a polymerized material substantially derived from one or more dioxetane compounds of formula 1, as defined above, or from a composition one or more dioxetane compounds of formula 1, as defined above, and/or one or more of said dioxetane compounds of formula 1.

The invention further provides electrooptical systems of scattering type comprising one or more dioxetane compounds of formula 1, or a composition comprising one or more dioxetane compounds of formula 1, as defined above.

The invention is further useful for coating substrates with one or more of the dioxetane compounds of formula I, or compositions comprising one or more of said dioxetane compounds of formula I, as defined above.

In the foregoing and in the following examples, all temperatures are set forth uncorrected in degrees Celsius, and, unless stated otherwise, all parts and percentages are by weight.

EXAMPLE 1

Preparation of 4-[3-(3-Methyl-oxetan-3-ylmethoxy)-propoxy]-benzoyloxy-2-methylphenyl 4-[3-(3-methyl-oxetan-3-ylmethoxy)-propoxy]-benzoate

The title compound (4) was prepared according to the following reaction scheme:

1.02 Preparation of 3-[3-(4-Bromo-phenoxy)-propoxymethyl]-3-methyl-oxetane (2)

A mixture of 10 g of milled potassium hydroxide and 30 ml of dimethylsulfoxide was stirred for 5 minutes. Then, 20 g of 3-(4-bromo-phenoxy)-propan-1-ol (1) was added followed by 25 g of toluene-4-sulfonic acid 3-methyl-oxetan-3-ylmethyl ester (see: Yong-Hong et al., *Macromolecules* 1995, 28, 1673–80). The mixture was stirred for 16 hours at room temperature and then heated to 50° C. for one hour. 3 ml of methanol was added and stirring was continued for one hour at this temperature. After cooling, 100 ml of diethyl ether was added and the mixture was extracted twice with 80 ml of water and once with 40 ml of brine. After evaporation of the diethyl ether, 80 ml of dichloromethane was added. This solution was dried over magnesium sulphate and passed through a small silica pad. After evaporation, 21 g of the product (75%) was obtained as a clear oil.

1.03 Preparation of 4-[3-(3-Methyl-oxetan-3-ylmethoxy)-propoxy]-benzoic acid (3)

35 ml of 1 molair n-butyllithium in n-hexane was added dropwise to a solution of 25 g of 3-[3-(4-bromo-phenoxy)-propoxymethyl]-3-methyl-oxetane (2) in 120 ml of dry 1.01 Preparation of 3-(4-Bromo-phenoxy)-propan-1-ol (1)

A mixture of 87 g of 4-bromophenol, 27 g of sodium methanolate, 15 g of sodium iodide and 300 ml of butanone was stirred at room temperature until complete dissolution. 3-Chloro-1-propanol (42 ml) was added and the solution was refluxed for 16 hours. After cooling and filtration, the butanone was evaporated. The residue was partitioned between 500 ml of diethyl ether and 125 ml of water. After separation, the diethyl ether solution was extracted twice with 125 ml of a 10% sodium hydroxide solution and once with 125 ml of brine. After drying over magnesium sulphate, the diethyl ether was evaporated. The product (90 g, 78%) was obtained as a clear oil.

tetrahydrofuran cooled to −70° C. After the addition, the mixture was stirred for one hour at this temperature and then solid dry ice was added until complete saturation. Stirring was continued until the solution reached room temperature. 120 ml of diethyl ether and 100 ml of water were added. After separation, 36 ml of 2.5 N hydrochloric acid was added dropwise to the well stirred aqueous layer. The precipitate was washed with 150 ml of water and dried in a dessicator. A white powder (15 g, 67%) was obtained with a melting point of 102° C.

1.04 Preparation of 4-[3-(3-Methyl-oxetan-3-ylmethoxy)-propoxy]-benzoyloxy-2-methyl phenyl 4-[3-(3-methyl-oxetan-3-ylmethoxy)-propoxy]-benzoate (4) 2.1 g of N,N'-dicyclohexyl carbodiimide was added to a solution of 2.8 g of 4-[3-(3-Methyl-oxetan-3-- ylmethoxy)-propoxy]-benzoic acid (3), 0.6 g of methylhydroquinone and 0.1 g of 4-N,N-dimethylaminopyridine in 30 ml of dichloromethane, stirred in an ice bath. After stirring for 16 hours at room temperature, the mixture was filtered over a small amount of silica and recrystallised from 13 ml of ethanol. A white powder (2.2 g, 68%) was obtained with a melting point (m.p.) of 100° C. and a crystallization point (c.p.) of 27° C.

EXAMPLE 2

Preparation of 4-[6-(3-Methyl-oxetan-3-ylmethoxy)-hexyloxy]-benzoyloxyphenyl 4-[6-(3-methyl-oxetan-3-ylmethoxy)-hexyloxy]-benzoate The title compound (6) was prepared according to the following reaction scheme:

solution was added. The mixture was refluxed for 8 hours. After cooling, the aqueous solution was extracted with 50 ml of diethyl ether and neutralised by addition of 17 ml of 2.5N hydrochloric acid with vigorous stirring. The precipitate was washed with 100 ml of water and dried in a dessicator. 15 g of the product (84%) was obtained as a white powder with a melting point of 62° C.

2.02 Preparation of 4-[6-(3-Methyl-oxetan-3-ylmethoxy)-hexyloxy]-benzoyloxyphenyl 4-[6-(3-methyl-oxetan-3-ylmethoxy)-hexyloxy]-benzoate (6)

2.1 g of N,N'-dicyclohexyl carbodiimide was added to a solution of 3.2 g of 4-[6-(3-Methyl-oxetan-3-ylmethoxy)-hexyloxy]-benzoic acid (5), 0.55 g of hydroquinone and 0.12 g of 4-N,N-dimethylaminopyridine in 30 ml of dichloromethane, stirred in an ice bath. After stirring for 16 hours at room temperature, the mixture was filtered over a

6

2.01 Preparation of 4-[6-(3-Methyl-oxetan-3-ylmethoxy)-hexyloxy]-benzoic acid (5)

A mixture of 15 g of 3-[4-(3-bromo-propoxy)-butyl]-3-methyl-oxetane (see: Yong-Hong et al., *Macromolecules* 1995, 28, 1673–80), 11 g of ethyl 4-hydroxybenzoate, 12 g of potassium carbonate and 40 ml of butanone was refluxed for 16 hours. After cooling and filtration, the butanone was evaporated and a mixture of 100 ml of diethyl ether and 30 ml of water were added. After separation, the ethereal layer was extracted twice with 30 ml of a 10% sodium hydroxide solution and once with 30 ml of brine. After evaporation of the diethyl ether, 100 ml of a 5% potassium hydroxide small amount of silica and recrystallised from 25 ml of ethanol. 2.4 g of a white powder (66%) was obtained with a m.p. of 99° C. and a c.p. of 119° C.

EXAMPLES 3–6

Using one of the methods described in Examples 1 and 2 above the following compounds were prepared as listed in Table 1 below, together with their melting and crystallization points:

TABLE 1

| Example no. | n | R | m.p. (° C.) | c.p. (° C.) (from N phase) |
|---|---|---|---|---|
| 1 | 3 | $CH_3$ | 100 | 27 |
| 2 | 6 | H | 99 | 119 |
| 3 | 3 | H | 138 | — |
| 4 | 4 | $CH_3$ | 65 | 74 |
| 5 | 5 | $CH_3$ | 75 | 59 |
| 6 | 6 | $CH_3$ | 36 | 73 |

EXAMPLE 7

Photopolymerization of a Dioxetane of the Present Invention and Properties Thereof A mixture of 975 mg of 4-[4-(3-methyl-oxetan-3-ylmethoxy)-butyloxy]-benzoyloxy-2-methylphenyl 4-[4-(3-methyl-oxetan-3-ylmethoxy)-butyloxy]-benzoate and 25 mg Cyracure UVI-6990 was prepared.

Figure 1:
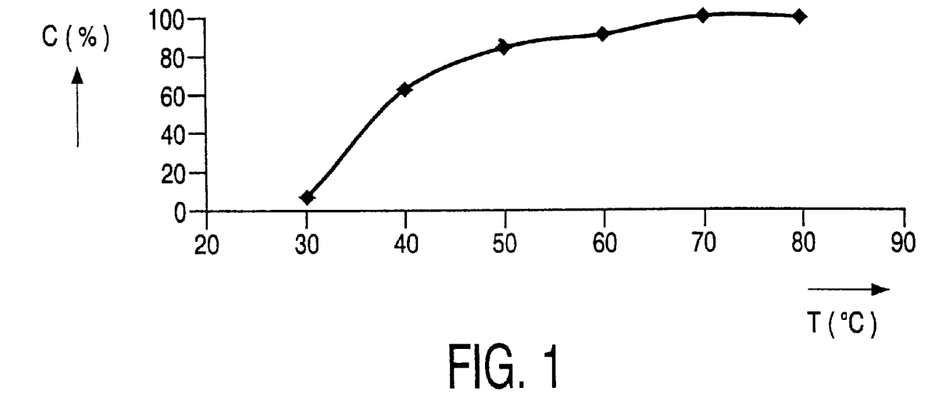
FIG. 1 shows the polymerization conversion C (in %) of a typical compound of the invention, 4-[4-(3-methyl-oxetan-3-ylmethoxy)-butyloxy]-benzoyloxy-2-methylphenyl 4-[4-(3-methyl-oxetan-3-ylmethoxy)-butyloxy]-benzoate, initiated by the photoinitiator Cyracure UVI-6990 and UV light, as a function of the temperature, T (in ° C.)

Small amounts of this mixture were photopolymerised in a photo DSC apparatus at various temperatures using a PL 10W lamp (7 mw/cm² at 365 nm). At temperatures above 40° C. good conversion was obtained with irradiation times of 15 minutes; see FIG. 1.

EXAMPLE 8

Stabilization of the Birefringence of a Dioxetane Polymer After Photoinitiated Polymerization at 60° C.

A 6 μm cell coated with rubbed polyimide was filled with a mixture of 975 mg of 4-[4-(3-methyl-oxetan-3-ylmethoxy)-butyloxy]-benzoyloxy-2-methylphenyl 4-[4-(3-methyl-oxetan-3-ylmethoxy)-butyloxy]-benzoate (see Example 4) and 25 mg Cyracure UVI-6990 at 80° C.

Figure 2:
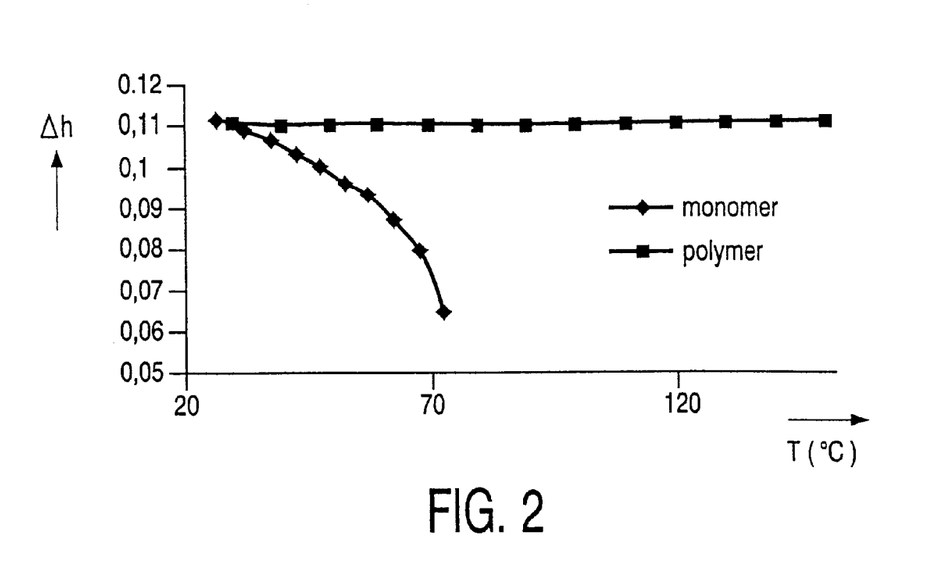
FIG. 2 shows the stabilization of the birefringence Δn of the same compound as in FIG. 1, after photoinitiated polymerization at 60° C. as a function of the temperature T (in ° C.).

A rapid alignment occurred and photopolymerization was performed at 60° C. for 30 minutes. The birefringence measured at 60° C. for the monomer was 0.09. After polymerization it increased to 0.11 and became completely temperature independent between 20 and 150° C. See FIG. 2. It appeared that by changing the polymerization temperature between 40 and 80° C. birefringent values between 0.07 and 0.11 were obtained for the polymer.

EXAMPLE 9

Spincoating of a Dioxetane Composition of the Invention

A mixture of 972 mg of 4-[6-(3-methyl-oxetan-3-ylmethoxy)-hexyloxy]-benzoyloxyphenyl 4-[6-(3-methyl-oxetan-3-ylmethoxy)-hexyloxy]-benzoate (Example 3) and 28 mg Cyracure UVI-6990 was prepared.

This mixture prepared as a 25/75 w/v solution in chlorobenzene was spincoated at 800 rpm on a glass substrate coated with rubbed polyimide. After heating the sample for 15 minutes at 60° C. for good alignment, it was stored at room temperature and no crystallization occurred for several days. Photopolymerization at 30° C. resulted in a 50% conversion (DSC) and formation of a layer with a birefringence of 0.11. Higher polymerisation conversion can be obtained in an annealing step at higher temperatures, for example at 150° C. for one hour, without changing the optical properties.

The present disclosure is to be considered as in all respects illustrative and not restrictive, the scope of the invention being indicated by the appended claims, and all changes which come within the meaning and range of equivalency are intended to be embraced therein.

What is claimed is:

1. A photopolymerizable liquid crystalline dioxetane compound having the general formula I:

wherein:

$R_1$ and $R_2$ are independently selected from straight or branched $C_1$–$C_4$ alkyl and hydrogen;

X and X' are independently selected from oxygen, sulfur, a single covalent bond, O—CO—, —CO—O—, and —O—CO—O—;

Y and Y' are spacer groups having each independently 1 to 30 carbon atoms (linear or branched), in which the carbon chain may be interrupted by sulfur in the thioether function, or, in which the carbon chain may be interrupted by oxygen in the ether function (i) when the X and X' and Z and Z' moieties are independently selected from oxygen, sulfur, O—CO, —CO—O—, and O—OCO—O—, or (ii) when the X and X' and Z and Z' moieties are single covalent bonds then the carbon chain is greater than 2 carbon atoms;

Z and Z' are independently selected from oxygen, sulfur, a single covalent bond, —O—CO—, —CO—O—, and —O—CO—O—; and M is any suitable mesogenic group.

2. A dioxetane compound according to claim 1, wherein Y and Y' are linear aliphatic alkylene chains of up to 30 carbon atoms, which may be each be branched by one or more methyl groups, or ethylene oxide $(C_2H_4O)_n$ chains having up to 30 carbon atoms, which may each contain one or more branched methyl groups, and M include groups of the formula II:

wherein:

Q and Q' are independently selected from the group of divalent saturated or unsaturated iso- or heterocyclic moieties, which may each be substituted by one, two or three equal or different fluoro, chloro, bromo, cyano, hydroxy, nitro, formyl, $C_{1-10}$ alkyl, $C_{1-10}$ alkoxy, $C_{1-10}$ alkoxycarbonyl, $C_{1-10}$ monoalkylaminocarbonyl, $C_{1-10}$ alkylcarbonyloxy groups, X" is X or X', or —CH₂—O—, —O—CH₂, —N=N—, —N=N(O)—, —CH₂S. —SCH₂—, —CO—O—, —O—CO—, or ethylene and P is 0, 1, 2 or 3.

3. A dioxetane compound according to claim 1 having the general formula Ia:

wherein R is methyl and n is 4, 5 or 6.

4. A composition comprising one or more dioxetane compounds as claims in claim 1, in conjunction with one or more liquid crystalline compounds selected from the group of normal non-polymerizable compounds and mono-oxetane monomers.

5. A composition according to claim 4, said composition containing one or more chiral compounds.

6. A crosslinked liquid crystalline (co)polymer product which is substantially derived from one or more dioxetane compounds as claimed in claim 1.

7. A liquid crystalline device characterized in that it incorporates a compound as claimed in claim 1.

8. A liquid crystalline device according to claim 7, which is a display cell comprising two opposite plates which are transparent to light electrodes of a material which is transparent to light on the sides of the plates facing each other, orientation layers on the electrodes, a sealing material between the plates, and a liquid crystalline material being filled into the space between the plates and the sealing material, said liquid crystalline material comprising a polymerizable liquid crystalline material substantially derived from on or more said compounds, which when polymerized forms a permanently oriented network, wherein said permanently oriented network is formed only locally in accordance with a desired pattern.

9. A liquid crystalline device according to claim 7, which is in the form of an anisotropic gel comprising a liquid crystalline (co)polymer product which is substantially derived from one or more said compounds, and a non-polymerizable low-molecular weight liquid crystalline material, wherein said liquid crystalline (co)polymer product forms a permanently oriented network in said non-polymerizable low-molecular weight liquid crystalline material.

10. A crosslinked liquid crystalline (co)polymer product which is substantially derived from a composition as claimed in claim 4.

11. A composition as claimed in claim 4, which when polymerized forms a permanently oriented network, wherein said permanently oriented network is formed only locally in accordance with a desired pattern.

12. A liquid crystalline device according to claim 9 wherein said non-polymerizable low-molecular weight liquid crystalline material in which said liquid crystalline (co)polymer product forms a permanently oriented network comprises a material selected from the group consisting of or mixtures thereof.

* * * * *